United States Patent [19]

Mori et al.

[11] Patent Number: 5,196,561
[45] Date of Patent: Mar. 23, 1993

[54] METHOD OF PRODUCING CARBONIC ACID ESTERS AND A CATALYST THEREFORE

[75] Inventors: Kenji Mori; Masao Tonosaki; Hidekazu Nakamura, all of Handa; Kenzo Yamamoto, Yokohama; Tsutomu Toida; Miki Tojima, both of Handa, all of Japan

[73] Assignee: JGC Corporation, Tokyo, Japan

[21] Appl. No.: 656,061

[22] PCT Filed: Jun. 13, 1990

[86] PCT No.: PCT/JP90/00768
§ 371 Date: Feb. 15, 1991
§ 102(e) Date: Feb. 15, 1991

[87] PCT Pub. No.: WO90/15791
PCT Pub. Date: Dec. 27, 1990

[30] Foreign Application Priority Data

Jun. 15, 1989 [JP] Japan .................. 1-150624
Feb. 26, 1990 [JP] Japan .................. 2-42404

[51] Int. Cl.$^5$ ............... C07C 68/02; C07C 68/00
[52] U.S. Cl. .................. 558/277; 558/260; 558/270; 558/274; 558/275
[58] Field of Search .......... 558/274, 277, 260, 275, 558/270

[56] References Cited

U.S. PATENT DOCUMENTS 3,846,468 11/1974 Perrotti et al. .......... 558/274
3,952,045 4/1976 Gaensler et al. .......... 558/277

Primary Examiner—Arthur C. Prescott
Attorney, Agent, or Firm—Cushman, Darby & Cushman

[57] ABSTRACT

Carbonic acid esters are important compounds as a gasoline extender, an octane number improver, an organic solvent and a reacting agent in place of phosgene for production of isocyanates, polycarbonates and various intermediates of agricultural chemicals and pharmaceuticals.

According to the present invention, carbonic acid esters can be prepared by reacting an alcohol with carbon monoxide and oxygen in the presence of a catalyst comprising a copper halide and a tertiary organophosphorus compound having phenyl group or alkyl group.

19 Claims, No Drawings

METHOD OF PRODUCING CARBONIC ACID ESTERS AND A CATALYST THEREFORE

FIELD OF THE INVENTION

Carbonic acid esters are important compounds as a gasoline extender, an octane number improver, an organic solvent and a reacting agent in place of phosgene for production of isocyanates, polycarbonates and various intermediates of agricultural chemicals and pharmaceuticals.

The present invention relates to a method of producing carbonic acid esters by oxidation-carbonylation of alcohols, and to a catalyst for producing carbonic acid esters.

DESCRIPTION OF THE PRIOR ART

As to methods of producing carbonic acid esters from alcohols, carbon monoxide and oxygen, liquid phase reaction using copper chloride as a catalyst is known. To improve the liquid phase method, numerous patents employing copper system catalysts or palladium system catalysts have been disclosed.

For example, Japanese Patent Provisional Publication No. Sho 50.40528(1975) discloses a method using an alcoholic (methanolic) solution of a catalyst system comprising copper chloride or copper bromide, and triarylphosphineoxide or a salt of organic phosphorus acids, phosphoric acids or phosphonic acids.

Furthermore, mentions are made on such methods as a method (Japanese Patent Provisional Publication No. Sho 54.24827(1979)) of using a catalyst comprising a cuprous halide and an alkali metal or an alkaline earth metal halide, a method (Japanese Patent Provisional Publication No. Sho 60.75447(1985)) of using a catalyst comprising palladium, a heteropolyacid and a nitrogen compound selected from a group consisting of nitric acid, nitrous acid esters and nitrogen oxide, and a method (Japanese Patent Provisional Publication No. Sho 62.81356(1987)) of using a catalyst system containing a hydrocarboxy copper halide, an imidazole compound, a pyridine compound or a cyclic amide.

However in the liquid phase method, there are such defects as (1) the activity of catalyst lowers remarkably due to water and carbon dioxide formed during the reaction; (2) materials for reaction equipments are corroded by dissolved state halides used as the catalyst, and (3) difficulties in separating reaction products and dissolved catalysts from effluent of reactors.

Japanese Patent Provisional Publication No. Sho 60.75447(1985) proposes employment of a carrier like active carbon, silica gel, alumina, etc. for metallic palladium or a palladium compound which constitutes one of components of the catalyst, however, the above mentioned defects are not always overcome.

As a method of solving these defects, researches on synthesis of carbonic acid esters by gas phase reaction have been conducted, and International Application Publication W087/07601 discloses a method of producing carbonic acid esters by gas phase reaction of an alcohol, carbon monoxide and oxygen in the presence of a catalyst carrying copper halides on a carrier (active carbon, alumina, titania, silica, etc.).

However, conventional catalyst systems are low in the activity or are required to be operated under severe reaction conditions in order to improve the yield.

The object of the present invention is to provide a method of producing carbonic acid esters from alcohol, carbon monoxide and oxygen, which is capable of maintaining an enhanced activity for a long period of time, and also to provide a catalyst for the production.

SUMMARY OF THE INVENTION

A method of producing carbonic acid esters according to the present invention is characterized by reacting an alcohol with carbon monoxide and oxygen in the presence of a catalyst containing a copper halide and a tertiary organophosphorus compound having phenyl group or alkyl group.

And, a catalyst for producing carbonic acid esters according to the present invention is characterized by comprising a copper halide and a tertiary organophosphorus compound having phenyl group or alkyl group.

DETAILED DESCRIPTION OF THE PREFERRED EMBODIMENTS

As for copper halides which are one of active ingredients of the catalyst, copper chloride, copper bromide and copper iodide are mentioned, and copper chloride may be used usually due to the cost and availability.

As for tertiary organophosphorus compounds having phenyl group or alkyl group, alkylarylphosphines like triphenylphosphine, triphenylphosphite and dimethylphenylphosphine, trialkylphosphites like trimethylphosphite and triethylphosphite, and trialkylphosphates like triethylphosphate and trimethylphosphate are mentioned.

The active ingredients may exist either in a form of a mixture of a copper halide and a tertiary organophosphorus compound having phenyl group or alkyl group, or in a form of a copper complex prepared by reacting a copper halide with a tertiary organophosphorus compound having phenyl group or alkyl group.

The catalyst comprising a copper halide and a tertiary organophosphorus compound having phenyl group or alkyl group may either be carried or not carried on a porous carrier, however, that of carried on a porous carrier exhibits a higher yield of carbonic acid esters per unit weight of the active ingredient comprising a copper halide and a tertiary organophosphorus compound.

As for porous carriers, those having surface areas of 30 m$^2$/g or above are preferred, and active carbon, titanium oxide, zirconium oxide, niobium oxide, magnesium oxide, silica and alumina are exemplified, and active carbon is the most preferred.

A copper halide and the above-mentioned tertiary organophosphorus compound may be carried on a carrier with a solvent at around the boiling point of the solvent. For example, it is conducted with ethanol solvent at 70°-80° C., and preferably under an inert gas (nitrogen, argon or helium) stream saturated with ethanol.

As a method of carrying a copper halide and a tertiary organophosphorus compound having phenyl group and alkyl group on a carrier, such manners are employable as the copper halide is carried firstly and then the tertiary organophosphorus compound is carried; the tertiary organophosphorus compound is carried firstly and then the copper halide is carried; and a copper complex prepared beforehand by reacting the copper halide with the tertiary organophosphorus compound is carried on a carrier. For example, in an ethanol solution of a copper halide is added a carrier so as the copper halide is carried, and then an ethanol solution of a tertiary organophosphorus compound is added to solidify copper halide-tertiary organophosphorus compound on the carrier. As another manner, an ethanol solution of a tertiary organophosphorus compound is firstly made contact with a carrier, and then an ethanol solution of a copper halide is made contact.

Amounts of the tertiary organophosphorus compound to be added are preferably 0.05–0.4 mol per copper atom mol in the copper halide.

When the catalyst is carried on a carrier, contents of the copper halide in the catalyst is preferably around 2–10 wt.% per carrier as copper in the copper halide.

After the copper halide-tertiary organophosphorus compound is fixed on a carrier, the solvent is removed. For example, removal of the solvent ethanol is performed by evaporation at 70°–80° C. under air or an inert gas atmosphere. In another manner, ethanol may be removed by applying vacuum at relatively low temperatures as 40° C.

When a complex is prepared beforehand with a copper halide and a tertiary organophosphorus compound, then the complex is carried on a carrier, the copper halide is dissolved in a solvent like ethanol or methylene chloride, and to the solution is added under an inert gas atmosphere a tertiary organophosphorus compound dissolved in a solvent like ethanol or methylene chloride to cause a reaction, and then the solvent is removed to obtain the copper complex.

The copper complex is carried on a carrier and fixed by dissolving thus obtained copper complex in such a solvent like chloroform, and the solution is applied on various porous carriers, or the complex is fixed on a carrier by mixing physically the complex wet with a solvent like a lower alcohol or in the absence of solvent, and then processing under an inert gas atmosphere (nitrogen, argon or helium) for stabilization.

As for copper complexes prepared with a copper halide and a tertiary organophosphorus compound, those represented by the following formula are especially preferred;

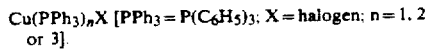

$Cu(PPh_3)_nX$ [$PPh_3 = P(C_6H_5)_3$; X = halogen; n = 1, 2 or 3].

The above-mentioned copper complex can be prepared with copper halides like cuprous chloride or cupric chloride and triphenyl phosphine. (refer to examples for preparing copper complexes)

Contents of the copper complex in the catalyst are to be around 2–10 wt.% per carrier as copper in the copper complex.

Catalysts with such copper complexes carried on carriers exhibit higher activities than a copper complex by itself in the synthesis of carbonic acid esters by oxidation-carbonylation of alcohols.

As to raw material alcohols, aliphatic alcohols having 1–4 carbon atoms, alicyclic alcohols and aromatic alcohols are employable. Examples thereof are methanol, ethanol, propylalcohol, butanol, cyclohexanol and benzylalcohol, and primary alcohols like methanol and ethanol are preferred.

Reaction conditions for producing carbonic acid esters from alcohols, carbon monoxide and oxygen are preferably reaction temperature of 70°–200° C. and reaction pressure of from atmospheric pressure to 15 kg/cm²G for the vapor phase reaction, and reaction temperature of 80°–150° C. and reaction pressure of 5–30 kg/cm²G for the liquid phase reaction.

Molar ratios of carbon monoxide and oxygen to alcohols like methanol or ethanol are preferably around 1.2–0.5 and 0.55–0.01 respectively ($CO/O_2$ ratio = 1/1–100/1).

The present invention will be explained concretely hereunder with examples, but the invention never be limited by the examples. [Comparative Example 1]

A test was conducted for a known catalyst carrying copper halide on a porous carrier.

Into a 500 ml (milliliter) flask, 8.465 grams of cupric chloride ($CuCl_2$) and 150 ml of ethanol were charged to make a solution. Then, 50 grams of an active carbon (surface area: 1000 m²/g; 4–16 mesh) were added to the solution and stirred. Ethanol was evaporated on a hot bath of 70°–80° C. to obtain Catalyst B1.

For the purpose of measuring activity of Catalyst B1 for dimethyl carbonate formation, a measurement was conducted using an ordinary atmospheric pressure fixed bed flow reactor under the following reaction conditions.

Into a stainless reactor tube having 10 mm inner diameter was packed 0.5 ml of Catalyst B1, and 6 ml/hr of methanol, 67 ml/min of carbon monoxide and 34 ml/min of oxygen were introduced into the tube under a vapor phase reaction conditions of 150° C. and atmospheric pressure to measure activity for dimethyl carbonate formation. The result is shown in Table 1.

EXAMPLE 1

Catalyst A1-A7 mentioned hereunder were prepared, and their activities for dimethyl carbonate formation were measured under the same conditions with Comparative Example 1, and the results are shown in Table 1.

Catalyst A1: Into a 500 ml flask equipped with a reflux condenser were charged 8.465 grams of cupric chloride ($CuCl_2$) and 150 ml of ethanol to make a solution, and 50 grams of an active carbon (surface area: 1000 m²/g; 4–16 mesh) were added to the solution. The solution was maintained at 70°–80 C. under a stream of nitrogen gas saturated with ethanol, and a solution prepared by dissolving 1.94 grams of triphenylphosphine as the tertiary organophosphorus compound in 100 ml of hot ethanol was poured slowly into the flask through the reflux condenser. The mixture was stirred vigorously under reflux for 2 hours. After completion of the reflux, the reflux condenser was removed and ethanol was evaporated to obtain Catalyst A1.

Catalyst A2: Catalyst A2 was prepared in the same manner with Catalyst A1 with the exception that 1.655 ml of triphenylphosphite was used as the tertiary organophosphorus compound in place of triphenylphosphine used for preparation of Catalyst A1.

Catalyst A3: Catalyst A3 was prepared in the same manner with Catalyst A1 with the exception that 0.754 ml of trimethylphosphite was used as the tertiary organophosphorus compound in place of triphenylphosphine used for preparation of Catalyst A1.

Catalyst A4: Catalyst A4 was prepared in the same manner with Catalyst A1 with the exception that 1.08 ml of triethylphosphite was used as the tertiary organophosphorus compound in place of triphenylphosphine used for preparation of Catalyst A1.

Catalyst A5: Catalyst A5 was prepared in the same manner with Catalyst A1 with the exception that 1.08 ml of triethylphosphate was used as the tertiary organophosphorus compound in place of triphenylphosphine used for preparation of Catalyst A1.

Catalyst A6: Catalyst A6 was prepared in the same manner with Catalyst A1 with the exception that 5.145 grams of triphenylphosphine was used as the tertiary organophosphorus compound.

Catalyst A7: Catalyst A7 was prepared in the same manner with Catalyst A1 with the exception that 3.175 grams of cupric chloride and 1.94 grams of triphenylphosphine were used.

As is shown clearly by the test results in Table 1, when an alcohol is reacted in a vapor phase with carbon monoxide and oxygen in the presence of a catalyst containing a copper halide and a tertiary organophosphorus compound having phenyl group or alkyl group, an enhanced activity of formation and selectivity for dimethyl carbonate are observed in comparison with the case of using the known catalyst B1 (catalyst of International Application Publication W087/07601) carrying only a copper halide on a carrier.

$m^2/g$) was used as a carrier. Its activity of formation for dimethyl carbonate measured by the same method with Comparative Example 1 was 0.106 mol/1-cat·h, which was 2.7 times of the catalyst of Comparative Example 3. Its selectivity for dimethyl carbonate was 43%, which was 2.7 times of the catalyst of Comparative Example 3.

As is shown clearly by the above test results, when an alcohol is reacted in a vapor phase with carbon monoxide and oxygen in the presence of a catalyst containing a copper halide and a tertiary organophosphorous compound having phenyl group or alkyl group, an enhanced activity of formation and selectivity for dimethyl carbonate are observed in comparison with a known catalyst composed of only a copper halide.

EXAMPLE 4

Synthesis tests for dimethyl carbonate were conducted using a high pressure fixed bed reactor. Into a

TABLE 1

| Catalyst | | | Mole ratio of organo-phosphorus compound/Cu | Dimethylcarbonate Formation | | | |
|---|---|---|---|---|---|---|---|
| | Cu content wt. % | Tertiary organo-phosphorus compound | | Activity of formation mol/1 – cat · h | Relative activity of formation *1 | Selectivity % | Relative selectivity *2 |
| B1 | 8 | none | 0 | 0.70 | 1.0 | 32 | 1.0 |
| A1 | 8 | triphenylphosphine | 0.12 | 2.01 | 2.9 | 70 | 2.2 |
| A2 | 8 | triphenylphosphite | 0.10 | 1.39 | 2.0 | 55 | 1.7 |
| A3 | 8 | trimethylphosphite | 0.10 | 1.34 | 1.9 | 65 | 2.0 |
| A4 | 8 | triethylphosphite | 0.10 | 1.38 | 2.0 | 62 | 1.9 |
| A5 | 8 | triethylphosphate | 0.10 | 1.32 | 1.9 | 62 | 1.9 |
| A6 | 8 | triphenylphosphine | 0.31 | 1.64 | 2.3 | 56 | 1.8 |
| A7 | 3 | triphenylphosphine | 0.31 | 2.09 | 3.0 | 74 | 2.3 |

*1: Activity of formation relative to 1.0 of Catalyst B1
*2: Selectivity relative to 1.0 of Catalyst B1

COMPARATIVE EXAMPLE 2

Catalyst B2 (copper content 8 wt.%) was prepared in the same manner with Comparative Example 1 with the exception that an alumina (surface area: 150 $m^2/g$) was used as a carrier. Its activity of formation for dimethyl carbonate measured by the same method with Comparative Example 1 was 0.043 mol/1-cat·h. Its selectivity for dimethyl carbonate was 18%.

EXAMPLE 2

Catalyst A8 (copper content 8 wt.%; mole ratio of organophosphorus compound/Cu =0.12) was prepared in the same manner with Catalyst A1 of Example 1 with the exception that an alumina (surface area: 150 $m^2/g$) was used as a carrier. Its activity of formation for dimethyl carbonate measured by the same method with Comparative Example 1 was 0.247 mol/1.cat·h, which was 5.7 times of the catalyst of Comparative Example 2. Its selectivity for dimethyl carbonate was 61%, which was 3.4 times of the catalyst of Comparative Example 2.

COMPARATIVE EXAMPLE 3

Catalyst B3 (copper content 8 wt.%) was prepared in the same manner with Comparative Example 1 with the exception that titanium oxide (surface area: 30 $m^2/g$) was used as a carrier. Its activity of formation for dimethyl carbonate measured by the same method with Comparative Example 1 was 0.040 mol/1-cat·h. Its selectivity for dimethyl carbonate was 16%.

EXAMPLE 3

Catalyst A9 (copper content 8 wt.%; mole ratio of organophosphorus compound/Cu =0.12) was prepared in the same manner with Catalyst A1 of Example 1 with the exception that titanium oxide (surface area: 30 stainless reactor tube having 12 mm inner diameter was packed respectively 7 ml of Catalyst A10–A19 mentioned below. To the tube were introduced 5 g/hr of methanol, 57.8 ml/min of carbon monoxide and 3.6 ml/min of oxygen under vapor phase reaction conditions of 6 kg/cm$^2$G and 150° C. to measure activities for dimethyl carbonate (DMC) formation. The results after 5 hours from the start of reaction are shown in Table 2.

Catalyst A10: Into a 500 ml flask equipped with a reflux condenser were charged 13.44 grams of cupric chloride and 150 ml of ethanol to make a solution. The solution was maintained at 70°–80C. under an inert gas (nitrogen) stream. Then, 39.35 grams of triphenylphosphine [P(C$_6$H$_5$)$_3$ abbreviated as PPh3]dissolved in 300 ml of ethanol were poured slowly and stirred for 2 hours under reflux. After completion of the reflux, the reaction product washed well with hot ethanol and filtered to obtain a complex represented by a formula Cu(PPh$_3$)Cl as Catalyst A10.

Catalyst A12: To 3.751 grams of a complex obtained in the same manner with Catalyst A10 were added 20 grams of an active carbon (surface area: 1000 $m^2/g$; 4.16 mesh) and a small amount of ethanol as a solvent, and mixed. After drying, the mixture was treated under an inert gas stream at 250° C. for 3 hours to obtain Catalyst A11.

Catalyst A12: To 3.751 grams of a complex obtained in the same manner with Catalyst A10 were added 20 grams of the active carbon used in Catalyst A11 and a small amount of ethanol as a solvent, and mixed. After drying, the mixture was treated under an inert gas stream at 300° C. for 3 hours to obtain Catalyst A12.

Catalyst A13: To 1.705 grams of a complex obtained in the same manner with Catalyst A10 were added 20 grams of the active carbon used in Catalyst A11 and a small amount of ethanol as a solvent, and mixed. After drying, the mixture was treated under an inert gas stream at 250° C. for 3 hours to obtain Catalyst A13.

Catalyst A14: To 5.114 grams of a complex obtained in the same manner with Catalyst A10 were added 20 grams of the active carbon used in Catalyst A11 and a small amount of ethanol as a solvent, and mixed. After drying, the mixture was treated under an inert gas stream at 250° C. for 3 hours to obtain Catalyst A14.

Catalyst A15: To 6.820 grams of a complex obtained in the same manner with Catalyst A10 were added 20 grams of the active carbon used in Catalyst A11 and a small amount of ethanol as a solvent, and mixed. After drying, the mixture was treated under an inert gas stream at 250° C. for 3 hours to obtain Catalyst A15.

Catalyst A16: To 3.751 grams of a complex obtained in the same manner with Catalyst A10 were added 20 grams of titanium oxide and a small amount of ethanol as a solvent, and mixed. After drying, the mixture was molded and treated under an inert gas stream at 250° C. for 3 hours to obtain Catalyst A16.

Catalyst A17: To 6.252 grams of a complex obtained in the same manner with Catalyst A10 were added 20 grams of zirconium oxide and a small amount of ethanol as a solvent, and mixed. After drying, the mixture was molded and treated under an inert gas stream at 250° C. for 3 hours to obtain Catalyst A17.

Catalyst A18: To 6.252 grams of a complex obtained in the same manner with Catalyst A10 were added 20 grams of niobium oxide and a small amount of ethanol as a solvent, and mixed. After drying, the mixture was molded and treated under an inert gas stream at 250° C. for 3 hours to obtain Catalyst A18.

Catalyst A19: To 3.751 grams of a complex obtained in the same manner with Catalyst A10 were added 20 grams of silica and a small amount of ethanol as a solvent, and mixed. After drying, the mixture was molded and treated under an inert gas stream at 250° C. for 3 hours to obtain Catalyst A19:

COMPARATIVE EXAMPLE 4

By using 3.175 grams of cupric chloride in Comparative Example 1 and in the same manner with Comparative Example 1, Catalyst B4 was obtained. Its activity of formation for dimethyl carbonate was measured in the same manner with Example 4. Result obtained after 5 hours from the start of reaction is shown in Table 2.

TABLE 2

| Catalyst | | Amount of complex charged g | Yield of DMC % *2 | Yield of DMC per unit amount of complex %/g |
|---|---|---|---|---|
| | Carrier | Content of Cu % *1 | | |
| B4 | Active carbon | 3.0 | — | 1.8 | — |
| A10 | None | — | 4.1 | 10.7 | 2.6 |
| A11 | Active carbon | 3.3 | 0.584 | 9.6 | 16.4 |
| A12 | Active carbon | 3.3 | 0.584 | 9.2 | 15.8 |
| A13 | Active carbon | 1.5 | 0.291 | 4.5 | 15.5 |
| A14 | Active carbon | 4.5 | 0.753 | 10.6 | 14.1 |
| A15 | Active carbon | 6.0 | 0.992 | 10.5 | 10.6 |
| A16 | Titanium oxide | 3.3 | 1.026 | 11.4 | 11.1 |
| A17 | Zirconium oxide | 5.5 | 1.858 | 9.8 | 5.27 |
| A18 | Niobium oxide | 5.5 | 1.858 | 16.6 | 8.93 |

TABLE 2-continued

| Catalyst | | Amount of complex charged g | Yield of DMC % *2 | Yield of DMC per unit amount of complex %/g |
|---|---|---|---|---|
| | Carrier | Content of Cu % *1 | | |
| A19 | Silica | 3.3 | 0.426 | 4.1 | 9.62 |

*1: Weight ratio of Cu per carrier

*2: Yield of DMC = $\frac{\text{Amount of methanol consumed for DMC formation}}{\text{Amount of methanol charged}} \times 100$ DMC is obtained more effectively by using a catalyst containing a complex represented by the formula $Cu(PPh_3)Cl$ when compared with the case using a known catalyst B4 (catalyst in International Application Publication W087/07601) carrying only $CuCl_2$ on a carrier. Though a high yield of DMC is obtained when Catalyst A10 composed only of a complex represented by the formula $Cu(PPh_3)Cl$, however, catalysts carried on carriers are superior from the viewpoints of yield of DMC per unit amount of the complex.

EXAMPLE 5

Synthesis tests for dimethyl carbonate were conducted with Catalysts A20–A36 mentioned below using a high pressure fixed bed reactor.

Into a stainless reactor tube having 12 mm inner diameter was packed 7 ml of respective catalyst. To the tube were introduced 5 g/hr of methanol, 57.8 ml/min of carbon monoxide and 3.6 ml/min of oxygen under vapor phase reaction conditions of 6 kg/cm$^2$G and 150° C. to measure activities for dimethyl carbonate formation. Yields of dimethyl carbonate after 5 hours from the start of reaction are shown in Table 3.

Catalyst A20: Into a flask equipped with a reflux condenser were charged 4.90 grams of cuprous chloride (CuCl) and 100 ml of methylene chloride to make a solution, and the solution was maintained at around 10° C. under an inert gas (nitrogen) stream. Then, 26.2 grams of triphenylphosphine (PPh3) dissolved in 100 ml of methylene chloride were poured slowly into the solution and the reaction was continued under agitation for 2 hours. After the reaction was completed, the reaction product was washed with hot ethanol and 5% aqueous ammonia, then filtered to obtain a complex represented by a formula $Cu(PPh_3)_2Cl$ as Catalyst A20.

Catalyst A21: To 5.89 grams of the complex $Cu(PPh_3)_2Cl$ obtained in the same manner with Catalyst A20 were added 20 grams of an active carbon (surface area 1000 m$^2$/g; 4.16 mesh) and a small amount of ethanol as a solvent, and mixed. After drying, the mixture was treated under an inert gas stream at 250° C for 3 hours to obtain Catalyst A21.

Catalyst A22: To 5.89 grams of the complex $Cu(PPh_3)_2Cl$ obtained in the same manner with Catalyst A20 were added 20 grams of the active carbon used in Catalyst A21 and a small amount of ethanol as a solvent, and mixed. After drying, the mixture was treated under an inert gas stream at 330° C. for 3 hours to obtain Catalyst A22.

Catalyst A23: To 5.89 grams of the complex $Cu(PPh_3)_2Cl$ obtained in the same manner with Catalyst A20 were added 20 grams of the active carbon used in Catalyst A21 and a small amount of ethanol as a solvent, and mixed. After drying, the mixture was treated under an inert gas stream at 390° C. for 3 hours to obtain Catalyst A23.

Catalyst A24: To 9.82 grams of the complex Cu(PPh3)2Cl obtained in the same manner with Catalyst A20 were added 20 grams of the active carbon used in Catalyst A21 and a small amount of ethanol as a solvent, and mixed. After drying, the mixture was treated under an inert gas stream at 250° C. for 3 hours to obtain Catalyst A24.

Catalyst A25: Into a flask equipped with a reflux condenser were charged 4.90 grams of cuprous chloride (CuCl) and 100 ml of methylene chloride to make a solution, and the solution was maintained at around 40° C. under an inert gas (nitrogen) stream. Then, 39.3 grams of triphenylphosphine (PPh3) dissolved in 100 ml of methylene chloride were poured slowly into the solution, and the reflux was continued under agitation for 2 hours. After the reflux was completed, the reaction product was washed with hot ethanol and 5% aqueous ammonia, then filtered to obtain a complex having a structure of Cu(PPh3)3Cl as Catalyst A25.

Catalyst A26: To 8.36 grams of the complex Cu(PPh3)3Cl obtained in the same manner with Catalyst A25 were added 20 grams of the active carbon used in Catalyst A21 and a small amount of ethanol as a solvent, and mixed. After drying, the mixture was treated under an inert gas stream at 330° C. for 3 hours to obtain Catalyst A26.

Catalyst A27: Into a flask equipped with a reflux condenser were charged 11.2 grams of cupric bromide (CuBr2) and 100 ml of ethanol to make a solution, and the solution was maintained at 70°-80° C. under an inert gas stream. Then, 20.0 grams of triphenylphosphine (PPh3) dissolved in 100 ml of hot ethanol were poured slowly into the solution, and refluxed for 2 hours under agitation. After completion of the reflux, the reaction product was washed with hot ethanol, then filtered to obtain a complex represented by a formula Cu(PPh3)Br as Catalyst A27.

Catalyst A28: To 3.83 grams of the complex Cu(PPh3)Br obtained in the same manner with Catalyst A27 were added 20 grams of the active carbon used in Catalyst A21 and a small amount of ethanol as a solvent, and mixed. After drying, the mixture was treated under an inert gas stream at 330° C. for 3 hours to obtain Catalyst A28.

Catalyst A29: Into a flask equipped with a reflux condenser were charged 7.00 grams of cuprous bromide (CuBr) and 100 ml of methylene chloride to make a solution and the solution was maintained at around 10° C. under an inert gas stream. Then, 26.2 grams of triphenylphosphine (PPh3) dissolved in 100 ml of methylene chloride were poured slowly into the solution and the reaction was continued for 2 hours under agitation. After completion of the reaction, the reaction product was washed with hot ethanol and 5% aqueous ammonia, then filtered to obtain a complex having a structure of Cu(PPh3)2Br as Catalyst A29.

Catalyst A30: To 6.31 grams of the complex Cu(PPh3)2Br obtained in the same manner with Catalyst A29 were added 20 grams of the active carbon used in Catalyst A21 and a small amount of ethanol as a solvent, and mixed. After drying, the mixture was treated under an inert gas stream at 250° C. for 3 hours to obtain Catalyst A30.

Catalyst A31: To 6.31 grams of the complex Cu(PPh3)2Br obtained in the same manner with Catalyst A29 were added 20 grams of the active carbon used in Catalyst A21 and a small amount of ethanol as a solvent, and mixed. After drying, the mixture was treated under an inert gas stream 340° C. for 3 hours to obtain Catalyst A31.

Catalyst A32: To 10.5 grams of the complex Cu(PPh3)2Br obtained in the same manner with Catalyst A29 were added 20 grams of the active carbon use in Catalyst A21 and a small amount of ethanol as a solvent, and mixed. After drying, the mixture was treated under inert gas stream at 340° C. for 3 hours to obtain Catalyst A32.

Catalyst A33: Into a flask equipped with a reflux condenser were charged 7.00 grams of cuprous bromide and 100 ml of methylene chloride to make a solution, and the solution was maintained at around 40° C. under an inert gas stream. Then, 39.3 grams of triphenylphosphine (PPh3) dissolved in 100 ml of methylene chloride were poured slowly into the solution and the solution was refluxed for 2 hours under agitation. After completion of the reflux, the reaction product was washed with hot ethanol and 5% aqueous ammonia, then filtered to obtain a complex represented by a formula Cu(PPh3)3Br as Catalyst A33.

Catalyst A34: To 8.79 grams of the complex Cu(PPh3)3Br obtained in the same manner with Catalyst A33 were added 20 grams of the active carbon used in Catalyst A21 and a small amount of ethanol as a solvent, and mixed. After drying, the mixture was treated under an inert gas stream at 340° C. for 3 hours to obtain Catalyst A34.

Catalyst A35: Into a flask equipped with a reflux condenser were charged 6.70 grams of cupric chloride, 15 grams of sodium iodide and 100 ml of ethanol to make a solution, and the solution was maintained at 70°-80° C. under an inert gas (nitrogen) stream. Then, 20 grams of triphenylphosphine (PPh3) dissolved in 100 ml of ethanol were poured slowly into the solution and refluxed for 2 hours under agitation. After completion of the reflux, the reaction product was washed with hot alcohol, then filtered to obtain a complex represented by a formula Cu(PPh3)I as Catalyst A35.

TABLE 3

| | Catalyst | | | | | Yield of |
|---|---|---|---|---|---|---|
| | Organo-phosphorus compound | Carrier: Treatment temperature | Content of Cu % *1 | Amount of complex charged g | Yield of DMC % *2 | DMC per unit amount of complex %/g |
| A20 | Cu(PPh3)2Cl | None | — | 4.2 | 1.8 | 0.43 |
| A21 | Cu(PPh3)2Cl | Active carbon 250° C. | 3.0 | 0.911 | 4.0 | 4.39 |
| A22 | Cu(PPh3)2Cl | Active carbon 330° C. | 3.0 | 0.911 | 6.5 | 7.14 |
| A23 | Cu(PPh3)2Cl | Active carbon 390° C. | 3.0 | 0.911 | 6.0 | 6.59 |
| A24 | Cu(PPh3)2Cl | Active carbon 250° C. | 5.0 | 1.480 | 7.2 | 4.86 |

TABLE 3-continued

| | Catalyst | | Content of Cu % *1 | Amount of complex charged g | Yield of DMC % *2 | Yield of DMC per unit amount of complex %/g |
|---|---|---|---|---|---|---|
| | Organo-phosphorus compound | Carrier: Treatment temperature | | | | |
| A25 | Cu(PPh$_3$)$_3$Cl | None | — | 4.6 | 1.2 | 0.26 |
| A26 | Cu(PPh$_3$)$_3$Cl | Active carbon 330° C. | 3.0 | 1.179 | 5.6 | 4.39 |
| A27 | Cu(PPh$_3$)Br | None | — | 4.3 | 10.9 | 2.52 |
| A28 | Cu(PPh$_3$)Br | Active carbon 330° C. | 3.0 | 0.611 | 8.0 | 13.1 |
| A29 | Cu(PPh$_3$)$_2$Br | None | — | 4.7 | 1.6 | 0.34 |
| A30 | Cu(PPh$_3$)$_2$Br | Active carbon 250° C. | 3.0 | 0.936 | 5.0 | 5.34 |
| A31 | Cu(PPh$_3$)$_2$Br | Active carbon 340° C. | 3.0 | 0.936 | 7.5 | 8.01 |
| A32 | Cu(PPh$_3$)$_2$Br | Active carbon 340° C | 5.0 | 1.520 | 8.2 | 5.39 |
| A33 | Cu(PPh$_3$)$_3$Br | None | — | 4.9 | 1.2 | 0.24 |
| A34 | Cu(PPh$_3$)$_3$Br | Active carbon 340° C. | 3.0 | 1.179 | 4.5 | 3.82 |
| A35 | Cu(PPh$_3$)I | None | — | 4.3 | 2.3 | 0.53 |
| A36 | Cu(PPh$_3$)I | Active carbon 380° C. | 3.0 | 0.652 | 4.0 | 6.13 |
| A37 | Cu(PPh$_3$)$_2$Cl | TiO$_2$:250° C. | 3.0 | 1.802 | 2.0 | 1.11 |
| A38 | Cu(PPh$_3$)$_2$Cl | ZrO$_2$:250° C. | 3.0 | 3.240 | 4.1 | 1.26 |
| A39 | Cu(PPh$_3$)$_2$Cl | Nb$_2$O$_5$:250° C. | 3.0 | 3.230 | 4.8 | 1.49 |

Catalyst A36: To 4.28 grams the complex Cu(PPh$_3$)I obtained in the same manner with Catalyst A35 were added 20 grams of the active carbon used in Catalyst A21 and a small amount of ethanol as a solvent and mixed. After drying, the mixture was treated under an inert gas stream at 380° C. for 3 hours to obtain Catalyst A36.

Catalyst A37: To 5.89 grams of the complex obtained in the same manner with Catalyst A20 were added 20 grams of titanium oxide and a small amount of ethanol, and mixed. After drying, the mixture was molded and treated under an inert gas stream at 250° C. for 3 hours to obtain Catalyst A37.

Catalyst A38: To 5.80 grams of the complex obtained in the same manner with Catalyst A20 were added 20 grams of zirconium oxide and a small amount of ethanol as a solvent, and mixed. After drying, the mixture was molded and treated under an inert gas stream at 250° C. for 3 hours to obtain Catalyst A38.

Catalyst A39: To 5.89 grams of the complex obtained in the same manner with Catalyst A20 were added 20 grams of niobium oxide and a small amount of ethanol as a solvent, and mixed. After drying, the mixture was molded and treated under an inert gas stream at 250° C. for 3 hours to obtain Catalyst A39.

It is noticed from Table 3 that copper complexes represented by the formula Cu(PPh$_3$)$_n$X [PPh$_3$ is P(C$_6$H$_5$)$_3$; X=halogen; n=1,2 or 3]are effective for production of carbonic acid esters, and especially that the yield per unit amount of copper complex increases remarkably for complexes carried on carriers.

EXAMPLE 6

Using Catalyst A7 which carried firstly a copper chloride and then triphenylphosphine and Catalyst A11 which carried a complex prepared beforehand by the reaction of a copper chloride and triphenylphosphine, activities for dimethyl carbonate (DMC) formation were investigated after 2 hours and 40 hours from the start of vapor phase reactions by the same method with Example 4, and the result are shown in Table 4.

TABLE 4

| Catalyst | | Yield of DME (%) *2 | |
|---|---|---|---|
| | Content of Cu wt. % *1 | 2 hours after start of reaction | 40 hours after start of reaction |
| A11 | 3.3 | 9.6 | 9.6 |
| A7 | 3.0 | 12.0 | 3.4 |

*1: Weight ratio of Cu per carrier

*2: Yield of DMC = $\dfrac{\text{Amount of methanol consumed for DMC formation}}{\text{Amount of methanol charged}} \times 100$ It is noticed that Catalyst A11 carrying on a porous carrier a complex prepared beforehand by reacting cupric chloride with triphenylphosphine possesses time stable capability for a longer period of in comparison with Catalyst A7 which carried firstly copper chloride and then triphenylphosphine.

EXAMPLE 7

Into an autoclave were charged 50 ml of methanol, 0.07 mol of oxygen, 0.149 mol of carbon monoxide, 0.078 mol of N$_2$ and 0.01 mol (3.61 g) of a complex (Catalyst A10) represented by the formula Cu(PPh$_3$)Cl, and a reaction was conducted under agitation for 6.5 hours under liquid phase reaction conditions of 13 kg/cm2G and 120° C. to obtain a DMC formation rate of 5.05 mol/l-MeOH g-mol complex·h.

On the other hand, a reaction was conducted in the same manner with the above using 0.01 mol (1.344 g) of a conventional CuCl$_2$ catalyst to obtain a DMC formation rate of 2.5 ml-l/l-MeOH·g-mol catalyst·h. From these results, it is noticed that Catalyst A10 is two times as active as CuCl$_2$.

EXAMPLE 8

The complex Cu(PPh3)Cl prepared in Example 7 was carried on an active carbon (surface area: 1000 m$^2$/g; 4.16 mesh) to prepare a catalyst (Cu content 3 wt.%), and 10 grams of the catalyst was used to conduct a reaction under the same conditions with Example 7. The amount of complex carried on the catalyst was 0.004 mol (1.46 g). As the result, a DMC formation rate of 24.2 mol/l.MeOH·g-mol complex·h was obtained, which was about 5 times of the case of Example 7 using singly a complex Cu(PPh₃)Cl.

EXAMPLE 9

Under the same reaction conditions with Example 7, a reaction was conducted using 0.01 mol (6.23 g) of Catalyst A20 [Cu(PPh₃)₂Cl: no carrier]. As the result, a DMC formation rate of 1.03 mol/1-MeOH·g-mol complex·h was obtained.

EXAMPLE 10

Under the same reaction conditions with Example 7, a reaction was conducted using 10 grams of Catalyst A22 [Cu(PPh₃)₂Cl; carried on active carbon]. The amount of complex carried on the catalyst was 0.0036 mol (2.27 g). As the result, a DMC formation rate of 7.20 mol/1-MeOH·g-mol complex·h was obtained, which was about 7 times of the case of Example 9 using Catalyst A 20 [Cu(PPh₃)₂Cl; no carrier].

EXAMPLE 11

Under the same reaction conditions with Example 7, a reaction was conducted using 0.01 mol (9.30 g) of Catalyst A33 [Cu(PPh₃)₃Br; no carrier]. As the result, a DMC formation rate of 0.85 mol/1-MeOH·g-mol complex·h was obtained.

EXAMPLE 12

Under the same reaction conditions with Example 7, a reaction was conducted using 10 grams of Catalyst A34 [Cu(PPh3)3 Br; carried on active carbon]. The amount of complex carried on the catalyst was 0.0033 mol (3.05 g). As the result, a DMC formation rate of 5.10 mol/1-MeOH·g-mol complex·h was obtained, which was 6 times of the case of Example 11 using Catalyst A33 [Cu(PPh₃)₃Br; no carrier].

EXAMPLE 13

Under the same reaction conditions with Example 7, a reaction was conducted using 0.01 mol (4.06 g) of Catalyst A27 [Cu(PPh₃)Br;no carrier]. As the result, a DMC formation rate of 5.28 mol/1-MeOH·g-mol complex·h was obtained.

EXAMPLE 14

Under the same reaction conditions with Example 7, a reaction was conducted using 10 grams of Catalyst A28 [Cu(PPh₃)Br; carried on active carbon](Cu content 3 wt.%). The amount of complex carried on the catalyst was 0.004 mol (1.61 g). As the result, a DMC formation rate of 31.9 mol/1-MeOH·g-mol complex·h was obtained, which was about 6 times of the case of Example 13 using Catalyst A27 [Cu(PPh₃)Br; no carrier].

It is noticed that a copper complex comprising a copper halide and a tertiary organophosphorus compound is effective for the liquid phase production of carbonic acid esters, and especially that a complex carried on a porous carrier is remarkably active.

INDUSTRIAL APPLICATION

It is possible to produce carbonic acid esters effectively.

We claim:

1. A method of producing carbonic acid esters by reacting an alcohol with carbon monoxide and oxygen in the presence of a catalyst, the catalyst comprising one of:

(a) a copper halide and a tertiary organophosphorus compound in a ratio of 0.05–0.4 mol of the tertiary organophosphorus compound per copper atom mol in the copper halide, the tertiary organophosphorus compound having a phenyl group or an alkyl group, and the copper halide and the tertiary organophosphorus compound being carried on a porous carrier; and (b) a copper complex having a molar ratio copper atom: the tertiary organophosphorus compound: halogen atom of 1:1–3: 1 prepared by reacting the copper halide with the tertiary organophosphorus compound, and the copper complex being carried on a porous carrier.

2. A method of producing carbonic acid esters according to claim 1, wherein the tertiary organophosphorus compound is selected from the group consisting of triphenylphosphine, triphenylphosphite, dimethylphenylphospine, trimethylphosphite, triethylphosphite, triethylphosphate and trimethylphosphate.

3. A method of producing carbonic acid esters according to claim 1, wherein the amount of copper in the catalyst is 2–10 wt. % per carrier.

4. A method of producing carbonic acid esters according to claim 1, wherein the porous carrier is selected from the group consisting of active carbon, titanium oxide, zirconium oxide, niobium oxide, magnesium oxide, silica and alumina.

5. A method of producing carbonic acid esters according to claim 1, wherein the alcohol is selected from the group consisting of aliphatic alcohols having 1–4 carbon atoms, alicyclic alcohols and aromatic alcohols.

6. A method of producing carbonic acid esters according to claim 1, wherein the method is carried out under temperatures of 70°–200° C. and pressures of 0–30 kg/cm²G.

7. A method of producing carbonic acid esters according to claim 1, in which the copper complex is represented by a formula Cu(PPh₃)ₙX, wherein PPh₃ is P(C₆H₅)₃: X is a halogen and n is 1, 2 or 3.

8. A method of producing dimethyl carbonate by reacting methanol with carbon monoxide and oxygen in the presence of a catalyst in a vapor phase under a reaction temperature of 70°–200° C. and a reaction pressure of from atmospheric pressure to 15 kg/cm²G, the catalyst comprising one of:

(a) a copper halide and a tertiary organophosphorus compound in a ratio of 0.05–0.4 mol of the tertiary organophosphorus compound per copper atom mol in the copper halide, the tertiary organophosphorus compound having a phenyl group or an alkyl group, and the copper halide and the tertiary organophosphorus compound being carried on a porous carrier; and (b) a copper complex having a molar ratio copper atom: tertiary organophosphorus compound: halogen atom of 1:1–3:1 prepared by reacting a copper halide with the tertiary organophosphorus compound, the copper complex being carried on a porous carrier.

9. A method of producing dimethyl carbonate according to claim 8, wherein the tertiary organophosphorus compound is selected from the group consisting of triphenylphosphine, triphenylphosphite, dimethylphenylphosphine, trimethylphosphite, triethylphosphite, triethylphosphate and trimethylphosphate.

10. A method of producing dimethyl carbonate according to claim 8, wherein the amount of copper in the catalyst is 2-10 wt. % per carrier.

11. A method of producing dimethyl carbonate according to claim 8, wherein the porous carrier is selected from the group consisting of active carbon, titanium oxide, zirconium oxide, niobium oxide, magnesium oxide, silica and alumina.

12. A method of producing dimethyl carbonate according to claim 8, wherein the molar ratio of carbon monoxide to methanol is 1:1.2-0.5 and the molar ratio of oxygen to carbon monoxide is 1:0.55-0.01.

13. A method of producing dimethyl carbonate according to claim 8, in which the copper complex is represented by a formula Cu(PPh$_3$)$_n$X, wherein PPh$_3$ is P(C$_6$H$_5$)$_3$; X is a halogen and n is 1, 2 or 3.

14. A method of producing dimethyl carbonate by reacting methanol with carbon monoxide and oxygen in the presence of a catalyst in a liquid phase under a reaction temperature of 80°-150° C. and a reaction pressure of 5-30 kg/cm$^2$G, the catalyst comprising one of:
(a) a copper halide and a tertiary organophosphorus compound in a ratio of 0.05-0.4 mol of the tertiary organosphosphorus compound per copper atom mol in the copper halide, the tertiary organophosphorus compound having a phenyl group or an alkyl group, and the copper halide and the tertiary organophosphorus compound are carried on a porous carrier; and
(b) a copper complex having a molar ratio copper atom: the tertiary organophosphorus compound: halogen atom of 1:1-3:1 prepared by reacting the copper halide with the tertiary organophosphorus compound, the copper complex being carried on a porous carrier.

15. A method of producing dimethyl carbonate according to claim 14, wherein the tertiary organophosphorus compound is selected from the group consisting of triphenylphosphine, triphenylphosphite, dimethylphenylphosphine, trimethylphosphite, triethylphosphite, triethylphosphate and trimethylphosphate.

16. A method of producing dimethyl carbonate according to claim 14, wherein the amount of copper in the catalyst is 2-10 wt. % per carrier.

17. A method of producing dimethyl carbonate according to claim 14, wherein the porous carrier is selected from the group consisting of active carbon, titanium oxide, zirconium oxide, niobium oxide, magnesium oxide, silica and alumina.

18. A method of producing dimethyl carbonate according to claim 14, wherein the molar ratio of carbon monoxide to methanol is 1:1.2-0.5 and the molar ratio of oxygen to carbon monoxide is 1:0.55-0.01.

19. A method of producing dimethyl carbonate according to claim 14, in which the copper complex is represented by a formula Cu(PPh$_3$)$_n$X, wherein PPh$_3$ is P(C$_6$H$_5$)$_3$; X is a halogen and n is 1, 2 or 3.

* * * * *

UNITED STATES PATENT AND TRADEMARK OFFICE
CERTIFICATE OF CORRECTION

PATENT NO. : 5,196,561
DATED : MARCH 23, 1993
INVENTOR(S) : MORI et al

It is certified that error appears in the above-identified patent and that said Letters Patent is hereby corrected as shown below:

Column 6 line 54 change "A12" to —A11—

Column 11 and 12 bottom of TABLE 3 add the following formula

\*1: Weight ratio of Cu per carrier $$*2: \text{Yield of DMC} = \frac{\text{Amount of methanol consumed for DMC formation}}{\text{Amount of methanol charged}} \times 100$$

Column 12 TABLE 4 change "DME" to —DMC—

Signed and Sealed this

Fifth Day of April, 1994

BRUCE LEHMAN

Attesting Officer    Commissioner of Patents and Trademarks